(12) United States Patent
Cheng

(10) Patent No.: US 11,376,023 B2
(45) Date of Patent: Jul. 5, 2022

(54) MEDICAL DEVICE HAVING AN ADAPTOR FOR ATTACHMENT TO A WORKING MEMBER

(71) Applicant: Gyrus ACMI, Inc., Southborough, MA (US)

(72) Inventor: Ming J. Cheng, West Warwick, RI (US)

(73) Assignee: Gyms Acmi, Inc., Westborough, MA (US)

( * ) Notice: Subject to any disclaimer, the term of this patent is extended or adjusted under 35 U.S.C. 154(b) by 539 days.

(21) Appl. No.: 15/993,772

(22) Filed: May 31, 2018

(65) Prior Publication Data
US 2019/0365390 A1    Dec. 5, 2019

(51) Int. Cl.
*A61B 17/16*   (2006.01)
*A61B 17/00*   (2006.01)

(52) U.S. Cl.
CPC ...... *A61B 17/1688* (2013.01); *A61B 17/1617* (2013.01); *A61B 17/1622* (2013.01); *A61B 2017/00477* (2013.01)

(58) Field of Classification Search
CPC . A61B 17/16; A61B 17/1613; A61B 17/1615; A61B 17/1617; A61B 17/1622; A61B 17/1688

USPC .......................................................... 606/80
See application file for complete search history.

(56) References Cited

U.S. PATENT DOCUMENTS

| 3,797,497 A * | 3/1974 | Crim ..................... B23Q 5/045 606/173 |
| 2012/0259337 A1* | 10/2012 | del Rio .............. A61B 17/1617 606/80 |
| 2015/0313610 A1 | 11/2015 | Edwards et al. |

* cited by examiner

*Primary Examiner* — Si Ming Ku
(74) *Attorney, Agent, or Firm* — Schwegman Lundberg & Woessner, P.A.

(57) ABSTRACT

Provided is a medical device comprising an adaptor having a slot and screw arrangement, the adaptor configured to be connectable to a handpiece; and an extension tube configured to be partially received within the adaptor, the extension tube configured to receive a drive shaft of a working member, wherein the slot and screw arrangement of the adaptor is configured to adjustably lock the extension tube along the drive shaft of the working member. The medical device further comprises a locking ring having one or more slots, the locking ring configured to receive a portion of a handpiece, wherein the one or more slots of the locking ring is configured to work together with a locking pin to lock and secure the drive shaft of the working member.

18 Claims, 7 Drawing Sheets

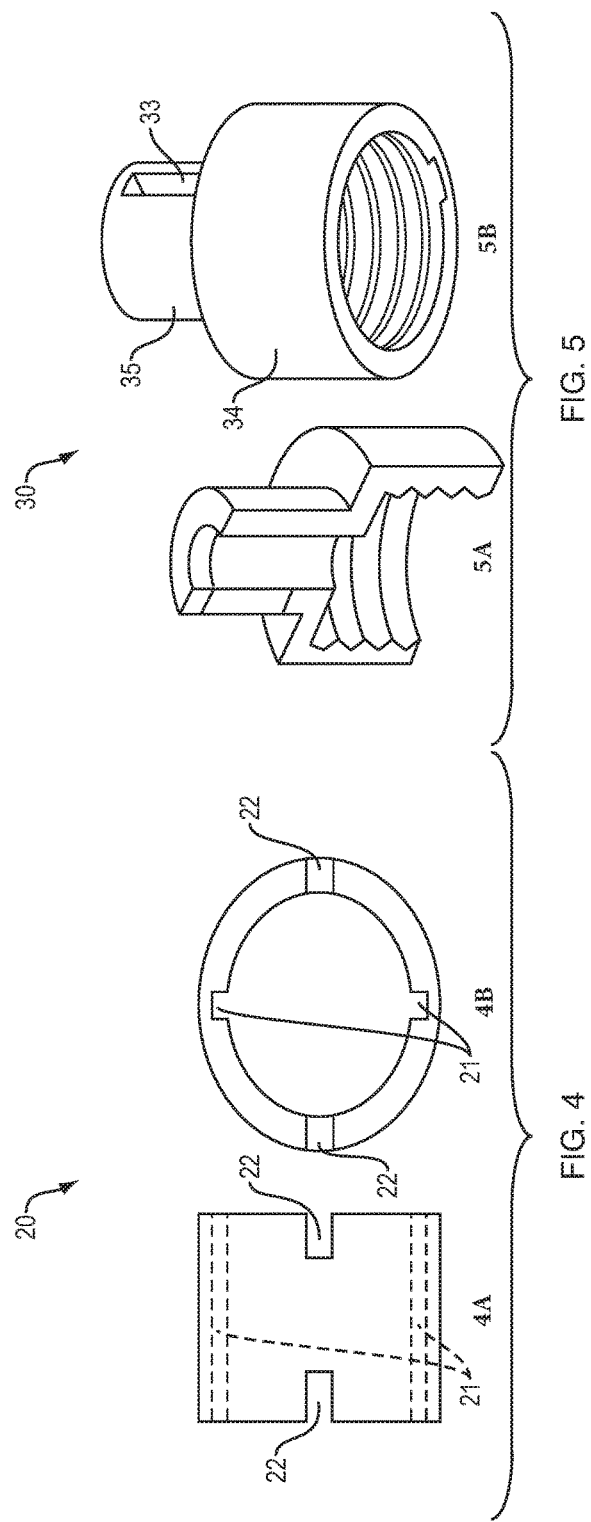

MEDICAL DEVICE HAVING AN ADAPTOR FOR ATTACHMENT TO A WORKING MEMBER

FIELD

The present disclosure relates generally to a medical device for nasal operations. More particularly, the present disclosure relates to a medical device having a handpiece and an adaptor configured to couple a working member with the handpiece for nasal operations.

BACKGROUND

In many surgical procedures, it is necessary or desirable to drill or abrade an object such as bone and tissue. In these situations, it is common to provide a rotary tool comprising a handle assembly having a high speed motor, and a coupling assembly at the distal end of the handle assembly for detachably connecting a working element such as a drill bit and a burr to the high speed motor, such that the working element can be turned by the high speed motor and then used for the desired purpose such as drilling or abrading bone and tissue. As such, there exists a need for a coupling assembly to detachably couple a high speed motor with a working member to achieve a desired outcome in a convenient and efficient way.

SUMMARY

In an embodiment, the present disclosure provides a medical device. In an embodiment, the medical device comprises a handpiece. In an embodiment, the medical device comprises a working member or element. In an embodiment, the medical device comprises an adaptor. In an embodiment, the medical device comprises an extension tube. In an embodiment, the medical device comprises a locking ring.

In an embodiment, the present disclosure provides a medical device. In an embodiment, the medical device comprises a handpiece, a working member or element, and an adaptor. In an embodiment, the medical device comprises a handpiece, a working member or element, an adaptor, and an extension tube. In an embodiment, the medical device comprises a handpiece, a locking ring, a working member or element, an adaptor, and an extension tube.

In an embodiment, the present disclosure provides a medical device comprising an adaptor having a slot and screw arrangement, the adaptor configured to be connectable to a handpiece; and an extension tube configured to be partially received inside the adaptor, the extension tube configured to partially receive a drive shaft of a working member, wherein the slot and screw arrangement is configured to adjustably lock the extension tube along the drive shaft of the working member. In an embodiment, the medical device further comprises a locking ring having one or more slots, the locking ring configured to receive a portion of the handpiece, wherein the one or more slots of the locking ring is configured to work together with a locking pin to lock the drive shaft of the working member.

In an embodiment, the present disclosure provides a medical device comprising a locking ring having one or more slots, the locking ring configured to receive a portion of a handpiece; an adaptor having a slot and screw arrangement, the adaptor configured to be connectable to the handpiece; and an extension tube configured to be partially received inside the adaptor, the extension tube configured to receive a drive shaft of a working member, wherein the slot and screw arrangement is configured to adjustably lock the extension tube along the drive shaft of the working member.

In an embodiment, the present disclosure provides a medical device comprising a handpiece; a working member having a drive shaft, the drive shaft configured to be operably connectable to the handpiece; a locking ring having one or more slots, the locking ring configured to lock the drive shaft of the working member; an adaptor having a slot and screw arrangement, the adaptor configured to be connectable to the handpiece; and an extension tube configured to provide support for the drive shaft of the working member, wherein the slot and screw arrangement is configured to adjustably lock the extension tube along the drive shaft of the working member.

In an embodiment, the present disclosure also provides a method of assembling a medical device as described herein.

In an embodiment, the present disclosure further provides a method of using a medical device as described herein.

BRIEF DESCRIPTION OF THE DRAWINGS

FIG. 4 is a side view and a front view of a locking ring in accordance with one aspect of the present disclosure;

FIG. 5 is a schematic view and a cutaway view of an adaptor in accordance with one aspect of the present disclosure;

DETAILED DESCRIPTION

Figure 1:
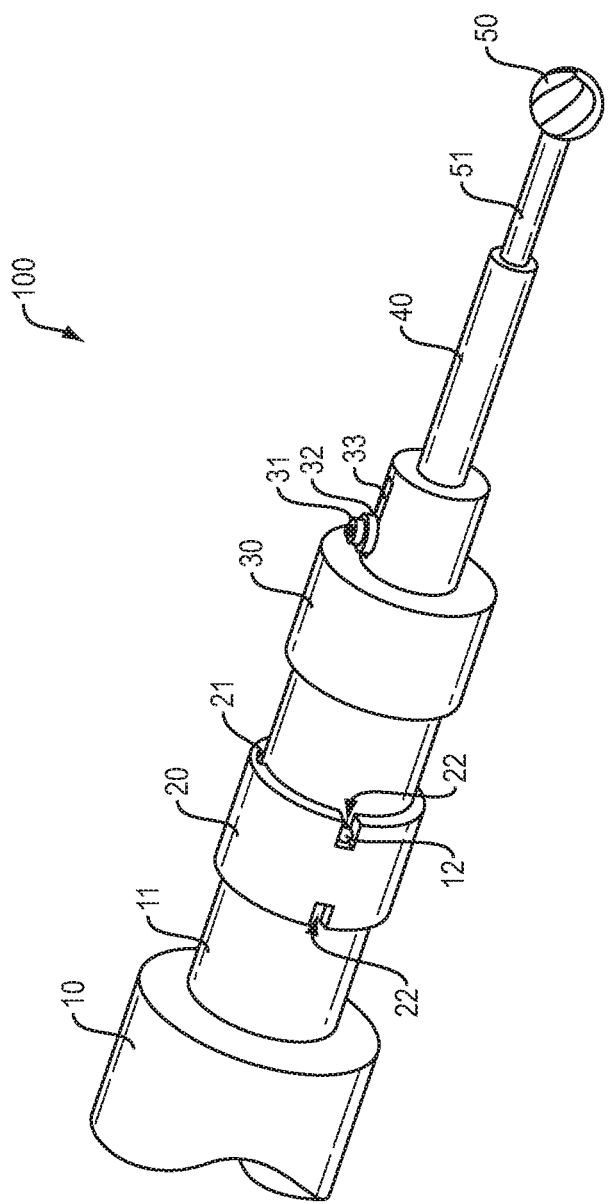
FIG. 1 is a partial schematic view of a medical device in accordance with one aspect of the present disclosure.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

The term "proximal" is herein used to mean a position or direction closest to a user of the device and is in a position or direction opposite to the term "distal".

The term "distal" is herein used to mean a position or direction furthest away from a user of the device and is a position or direction opposite to the term "proximal".

In an embodiment, the present disclosure provides a medical device. In an embodiment, the medical device comprises a handpiece. In an embodiment, the medical device comprises a working member or element. In an embodiment, the medical device comprises an adaptor. In an embodiment, the medical device comprises an extension tube. In an embodiment, the medical device comprises a locking ring.

In an embodiment, the present disclosure provides a medical device. In an embodiment, the medical device comprises a handpiece, a working member or element, and an adaptor. In an embodiment, the medical device comprises a handpiece, a working member or element, an adaptor, and an extension tube. In an embodiment, the medical device comprises a handpiece, a locking ring, a working member or element, an adaptor, and an extension tube.

In an embodiment, the present disclosure provides a medical device comprising an adaptor having a slot and screw arrangement, the adaptor configured to be connectable to a handpiece; and an extension tube configured to be partially received inside the adaptor, the extension tube configured to partially receive a drive shaft of a working member, wherein the slot and screw arrangement is configured to adjustably lock the extension tube along the drive shaft of the working member. In an embodiment, the medical device further comprises a locking ring having one or more slots, the locking ring configured to receive a portion of the handpiece, wherein the one or more slots of the locking ring is configured to work together with a locking pin to lock the drive shaft of the working member.

In an embodiment, the present disclosure provides a medical device comprising a locking ring having one or more slots, the locking ring configured to receive a portion of a handpiece; an adaptor having a slot and screw arrangement, the adaptor configured to be connectable to the handpiece; and an extension tube configured to be partially received inside the adaptor, the extension tube configured to receive a drive shaft of a working member, wherein the slot and screw arrangement is configured to adjustably lock the extension tube along the drive shaft of the working member.

In an embodiment, the present disclosure provides a medical device comprising a locking ring having one or more slots, the locking ring configured to receive a portion of a handpiece; an adaptor having a slot and screw arrangement, the adaptor configured to be connectable to the handpiece; and an extension tube configured to be partially received inside the adaptor, the extension tube configured to receive a drive shaft of a working member, wherein the one or more slots of the locking ring is configured to work together with a locking pin to lock the drive shaft of the working member.

In an embodiment, the present disclosure provides a medical device comprising a handpiece; a working member having a drive shaft, the drive shaft configured to be operably connectable to the handpiece; a locking ring having one or more slots, the locking ring configured to lock the drive shaft of the working member; an adaptor having a slot and screw arrangement, the adaptor configured to be connectable to the handpiece; and an extension tube configured to provide support for the drive shaft of the working member, wherein the slot and screw arrangement is configured to adjustably lock the extension tube along the drive shaft of the working member.

In the above embodiments when a locking pin is used to lock the driving shaft of a working member to a handpiece of a medical device such as Olympus high speed drill or other similar devices, a locking ring may be used to facilitate the locking pin to tighten and lock the drive shaft of the working member to the handpiece. In these embodiments, the locking ring may be configured to have one or more slots. The one or more slots may be configured to be open. The one or more slots may be configured to be hidden. The hidden slots are preferably configured to be straight across the circumference of the locking ring while the open slots are preferably configured to be short open slots. The one or more slots may be preferably configured to be two sets of slots with each set perpendicular to each other, and one set open, and the other set hidden. The one or more slots may be configured to be sized to receive a head of a locking pin. Also, the open slots are configured to be capable of securing the locking pin of the drive shaft in place while the device is in operation or use. In the above embodiments, the locking ring is configured to receive a portion of a handpiece. Or more particularly, it is configured to receive the distal portion of the handpiece. Or even more particularly, it is configured to be capable of sliding over the distal portion of the handpiece. Consequently, the diameter of the locking ring is configured to be larger than that of the distal portion of the handpiece. In the above embodiments, the diameter of the locking ring may be preferably configured to be the same throughout its whole length. In the above embodiments, the diameter of the locking ring may also vary if necessary. The locking ring may be made of any suitable materials such as polymeric and metallic materials. The locking ring may be preferably made of polymeric materials. The locking ring may be preferably made to be disposable even though it may also be made reusable.

In the above embodiments, the adaptor comprises a proximal or head section and a distal or tail section. The proximal section is configured to be detachably connectable to a distal end of the handpiece. The inside of the proximal section is preferably configured to be threaded to facilitate a connection with the distal end of the handpiece which is preferably threaded. Of course, other connection mechanisms such as snap fitting are also contemplated. The distal section is configured to have a screw and slot arrangement to allow a lock screw to move along a slot to lock the extension tube into a desirable position. The slot is configured to be open along the longitudinal direction of the adaptor, and can be easily sized and dimensioned as desired. As for the lock screw, it may be sized and dimensioned in accordance with the size and dimension of the slot. The adaptor may be made of any suitable materials such as polymeric or metallic materials. It may be preferably made of plastic materials or aluminum. The adaptor may be preferably made to be disposable even though it may be made reusable. Similarly, the lock screw may be made of any suitable materials such as polymeric or metallic materials. It may be preferably made of plastic materials or aluminum. It may be preferably made to be disposable even though it may be made reusable.

In the above embodiments, the extension tube is configured to be partially received within the adaptor, and extends towards the distal end of the medical device. Also, the extension tube is configured to partially receive a drive shaft of a working member. The diameter and the length of the extension tube may be configured in accordance with the flexibility need of the drive shaft of the working member. The length of the extension tube may account for up to two thirds of the distance from the distal end of the adaptor to the working member. Since the extension tube is configured to absorb a significant portion of vibration or torque that may be produced during an operation, it should be made to tightly receive the drive shaft of the working member, and yet to allow freedom of rotation together with the shaft to minimize friction with the drive shaft if necessary. The extension tube may be made of any suitable material. It is preferably made of plastic material. It is preferably made to be disposable.

In the above embodiments, the handpiece may be an Olympus high speed drill related handpiece. In the above embodiments, the handpiece may be from other companies. In the above embodiments, the handpiece may have a high speed motor. In the above embodiments, the drive shaft of the working member may be driven by a high speed motor in the handpiece. In the above embodiments, the working element or member may be a high speed drill bit or a high speed burr.

In an embodiment, the present disclosure also provides a method of assembling a medical device as described herein. More particularly, the method includes providing a medical device having a handpiece. The method includes connecting the handpiece with a drive shaft of a working member through the adaptor and the extension tube followed by locking the drive shaft through a locking pin. The method includes sliding the locking ring into a proper position to engage the locking pin, followed by rotating the locking ring to fully lock the drive shaft into a locked position. The method includes tightening the adaptor into the handpiece through known means. The method includes adjusting and tightening the extension tube through the lock screw.

In an embodiment, the present disclosure further provides a method of using a medical device as described herein. More particularly, a medical device as described herein may be preferably used to abrade bone or cut tissue for nasal operations on a subject. In an embodiment, the present disclosure also provides a method of minimizing or even eliminating chattering of a medical device during a nasal operation, the method including coupling an adaptor and an extension tube with a conventional working member and employing the coupled assembly to perform a nasal operation to minimize or eliminate chattering. The method may optionally comprise employing a locking ring to further facilitate the assembly of the medical device as described herein.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

FIG. 1 is a schematic view of a portion of a medical device in accordance with one aspect of the present disclosure. The medical device 100 of FIG. 1 includes a handpiece 10 (only partially shown), a locking ring 20, an adaptor 30, an extension tube 40, and a working member 50 (a burr). More particularly, the handpiece 10 is partially shown to have a distal end 11. The locking ring 20 has a hidden slot 21 and two open slots 22. The adaptor 30 has a lock screw 31, a lock nut 32, and a slot 33. The slot 33 is disposed at the distal or tail end of the adaptor 30, and the lock screw 31 is configured to be able to slide forward or backward along the slot 33 to adjust the position of the lock screw 31. The lock screw 31 can be tightened to the lock nut 32 to lock its position along the slot 33. The extension tube 40 is partially received within the adaptor 30. The working member burr 50 has a drive shaft 51. The drive shaft 51 is configured to be connectable through the distal end 11 of the handpiece 10 to a high speed motor housed inside the handpiece (not shown).

The medical device 100 may be assembled for a surgical operation through the following sequence: the locking ring 20 may slide over the distal end 11 of the handpiece 10. The drive shaft 51 of the working member 50 may then be inserted through the extension tube 40, then through the adaptor 30, and finally reach into a position inside the distal end of the handpiece to couple with the motor of the handpiece (not shown). Once the drive shaft 51 is in place, the locking pin 12, which generally comes with the handpiece, can then be used together with the locking ring 20 to smoothly and conveniently tighten and then lock the drive shaft 51 of the working member 50. Even more specifically, the steps include first engaging the hidden slot 21 with the head of the locking pin 12, then rotating the locking ring 20 to push the locking pin 12 along the slot 21 until the locking pin 12 is at a position to tightly lock the drive shaft 51 of the working member 50. Afterwards, it is preferable or desirable to loosen the locking ring 20 a little bit and to rotate it to place the locking pin 12 into the open slot 22 to ensure the locking pin 12 is always tightly secured by the slot 22 during a surgical operation. Once the drive shaft 51 is tightened, the adaptor 30 may then be tightened and secured to the handpiece by the known means such as snap fit or threaded coupling. Subsequently, the lock screw 31 can be adjustably tightened and secured to the nut 32 along the slot 33 in any desirable manner. It is of course possible or even desirable that the adaptor 30 and the extension tube 40 may be put together in advance. It may also be made as one piece through means known in the art.

Once an operation is finished, the medical device 100 may be easily disassembled in a reverse order as described above. More specifically, a working member having a drive shaft can be easily and conveniently released from the assembly by engaging the slot 21 of the locking ring 20 with the locking pin 12, and rotating the locking ring 20 in an opposite direction as described above to release the locking pin 12. Once the locking pin 12 is released, the drive shaft of the working member can then be easily pulled out for further disposal, and a new working member can be assembled in a manner as described above. The remaining individual components may then be disposed in any desirable way.

Figure 2:
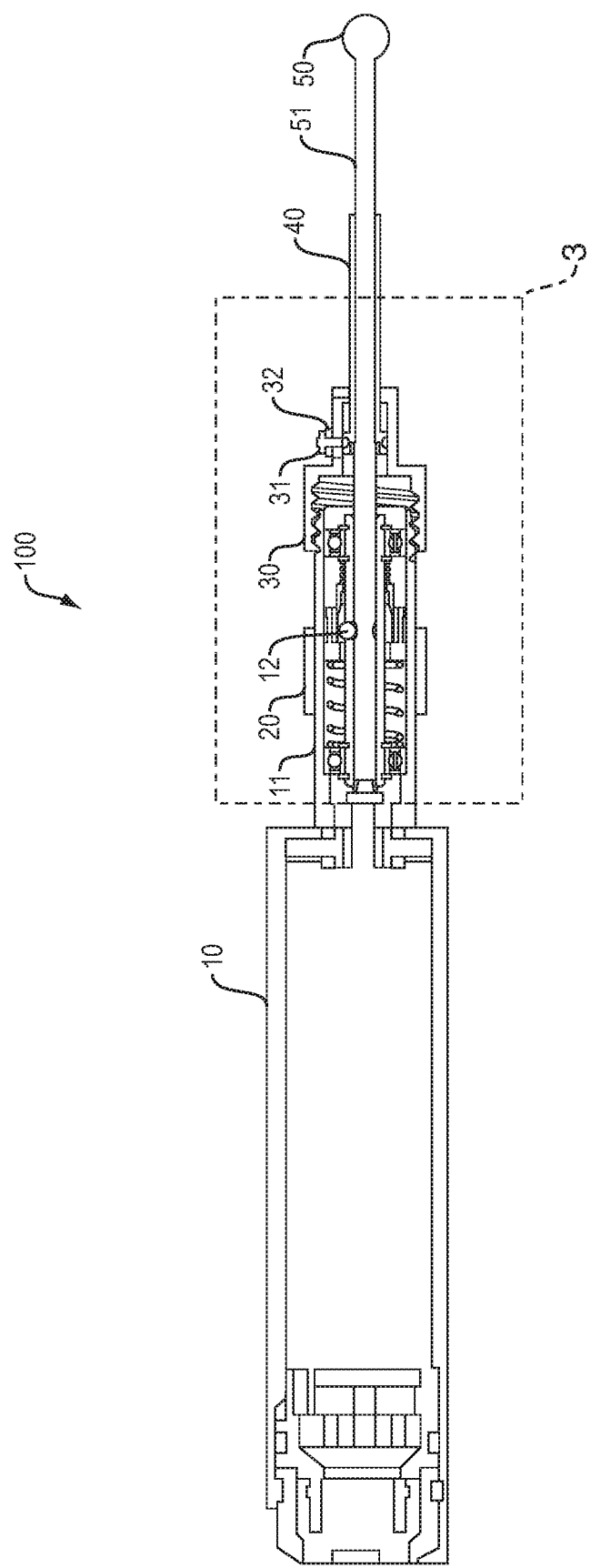
FIG. 2 is a partial sectional view of a medical device in accordance with one aspect of the present disclosure.

FIG. 2 is a partial sectional view of a medical device along its longitudinal direction in accordance with one aspect of the present disclosure. It has a handpiece 10, a distal end 11 of the handpiece 10, a locking pin 12, a locking ring 20, an adaptor 30, a locking screw 31, a locking nut 32, an extension tube 40, a drive shaft 51, and a working member 50. The locking ring 20 is configured to receive a portion of the distal end 11 of the handpiece 10. Put it additionally or alternatively, the locking ring 20 is configured to slide over the distal end 11 of the handpiece 10. The distal end 11 of the handpiece 10 of FIG. 2 is shown to have a threaded end for coupling with the threaded end of the adaptor 30. Still, other coupling mechanisms with the adaptor 30 such as snap fit or through high strength glue are also contemplated. The extension tube 40 is partially received within the adaptor 30. The outside portion of the extension tube 40 may depend upon the specific flexibility need of an operation. It may cover up to two thirds of the length of the drive shaft of the working member. That is: the length of the uncovered shaft may be up to about a half of the length of the extension tube covered portion. A more detailed description of the main features of the present disclosure is shown in FIG. 3.

Figure 3:
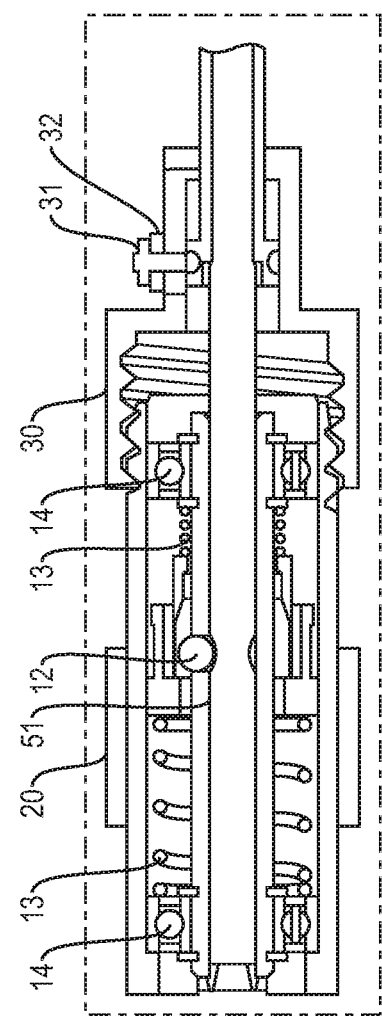
FIG. 3 is an enlarged sectional view of a portion of the medical device shown in FIG. 2.

FIG. 3 is an enlarged sectional view of the portion 3 as shown in FIG. 2. It shows the locking pin 12, the locking ring 20, the adaptor 30, the locking screw 31, the locking nut 32. It also shows springs 13 and bearings 14 within the distal end 11 of the handpiece 10. These components are used for coupling and rotating the drive shaft 51. It further shows the locking pin 12 tightly grips the drive shaft 51 of the working member 50. The locking pin 12 is secured into place by the slot 22 (FIG. 1). To release the drive shaft 51, all that has to be done is to reversely rotate the locking ring 20 to loosen the locking pin 12, and the drive shaft 51 is thus released and can be easily pulled out, and the handpiece is ready for exchange for a new working member. As for the lock screw and slot arrangement of the adaptor 30, it can be employed to easily adjust, tighten, and lock the extension tube along the drive shaft 51 of the working member.

FIG. 4 shows the front and side views of a locking ring 20 in accordance with one aspect of the present disclosure. More particularly, FIG. 4A is a side view, and FIG. 4B a front view. The locking ring 20 has a pair of hidden slots 21. The hidden slots 21 are preferably configured to be straight across the circumference of the locking ring 20. The pair of the hidden slots are preferably configured to be opposite and symmetrical along the longitudinal axis. Of course, they do not have to be hidden or symmetrical, and other designs are also contemplated so long as they can effectively engage a locking pin of the handpiece to lock and secure a drive shaft of a working member. The locking ring 20 is configured to have two pairs of short open slots 22, with one pair at the front and the other pair at the back. The pair of the open slots are preferably configured to be opposite and symmetrical along the longitudinal axis. Of course, they do not have to be open or symmetrical, and other designs are also contemplated so long as they can effectively secure the locking pin of the handpiece during a surgical operation. FIG. 4 shows that the set of hidden slots are perpendicular to the set of the open slots. However though, other types of configurations are also contemplated. The locking ring is configured to be slightly bigger than the distal end of the handpiece so that it can easily engage or disengage with the locking pin as needed during or after an operation. The locking ring is preferably made by plastic materials and preferably disposable.

FIG. 5 shows an adaptor 30 in schematic and cutaway views in accordance with one aspect of the present disclosure. More particularly, FIG. 5A is a cutaway view, and FIG. 5B a schematic view. The adaptor 30 is preferably configured to have a head portion 34 with threaded interior. The threaded head portion 34 is intended for an easy coupling with the distal end of a handpiece of the medical device. This type of coupling may be conveniently called threaded coupling. Of course, other configurations of the head portion are also contemplated so long as it can be tightly coupled to the distal portion of the handpiece. The dimension and configuration of the head portion 34 may be easily adjusted based on any coupling need with the distal end of the handpiece. The adaptor 30 may be configured to have a tail portion 35 with a slot 33. The slot 33 is open along the longitudinal direction of the drive shaft. The dimension and length of the slot 33 can be easily adjusted based on the need of flexibility of the extension tube or the drive shaft of the working member. If the extension tube is expected to control a longer portion of the drive shaft, the slot 33 may be made a bit longer. Otherwise, it can be made a bit shorter. It may cover up to two thirds of the drive shaft of the working member. The lock screw 31 and the lock nut 32 can of course be accordingly designed to be compatible with the slot 33 to tighten and secure the drive shaft of the working member. The screw and slow arrangement is known in the art, and can be adjusted in any suitable manner.

Figure 6:
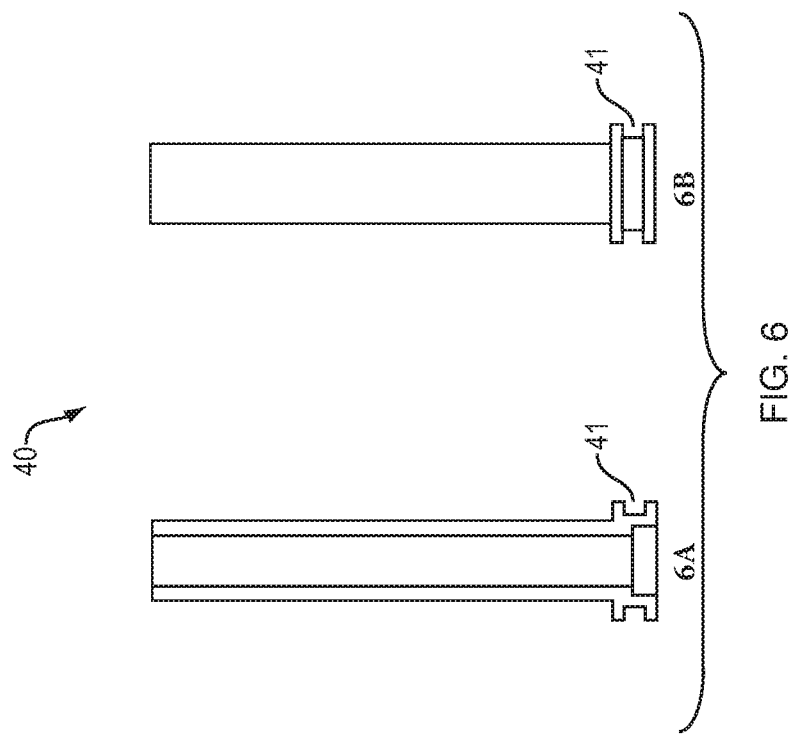
FIG. 6 is a top view and a sectional view of an extension tube in accordance with one aspect of the present disclosure.

FIG. 6 shows sectional and side views of an extension tube 40 in accordance with one aspect of the present disclosure. More particularly, FIG. 6A is a sectional view, and FIG. 6B is a side view. The extension tube 40 has a circular or annular groove 41 at its head for engagement with the tip of the lock screw. The extension tube can be easily moved along the drive shaft with the aid of the tip of the lock screw. The thickness of the extension tube 40 may vary based on the property or need of the drive shaft of the working member. The extension tube 40 is used to protect the drive shaft from becoming too heated or strained owing to its flexible feature. Put it slightly differently, the extension tube 40 is designed to absorb vibration and/or torque of the drive shaft of a working member during an operation so that the extension tube may be made to rotate with the drive shaft if necessary to minimize its friction with the drive shaft. It may also be understood to mean that the extension tube is intended to support the drive shaft of a working member for smooth rotation during an operation. It may also be understood to mean that the extension tube increases the bending flexibility of a drive shaft of a working member during an operation. The extension tube is thus preferably made with plastic or polymeric materials so that it can minimize vibration or chattering of the drive shaft of the working member.

Figure 7:
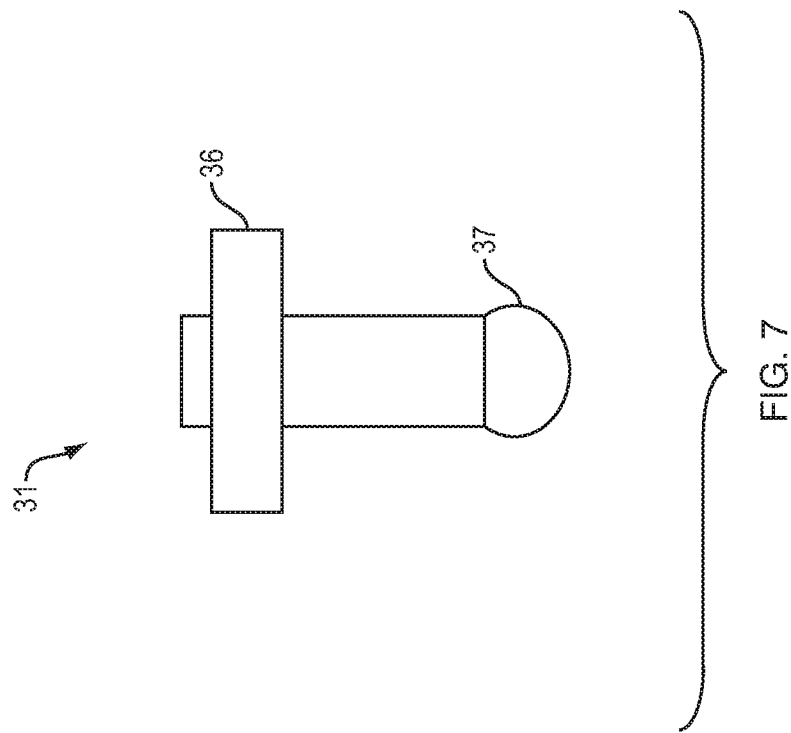
FIG. 7 is a schematic view of a lock screw in accordance with one aspect of the present disclosure.

FIG. 7 shows a lock screw 31 in accordance with one aspect of the present disclosure. Its tip 37 is designed to fit into the groove 41 of the extension tube 40, and can move the extension tube 40 along the slot 33 of the adaptor 30. It also has a head 36. Once placed in a desired location, the extension tube can then be locked into this position by the lock screw 31. The location can always be conveniently adjusted by the lock screw 31 whenever necessary or desirable due to this unique design.

Figure 8:
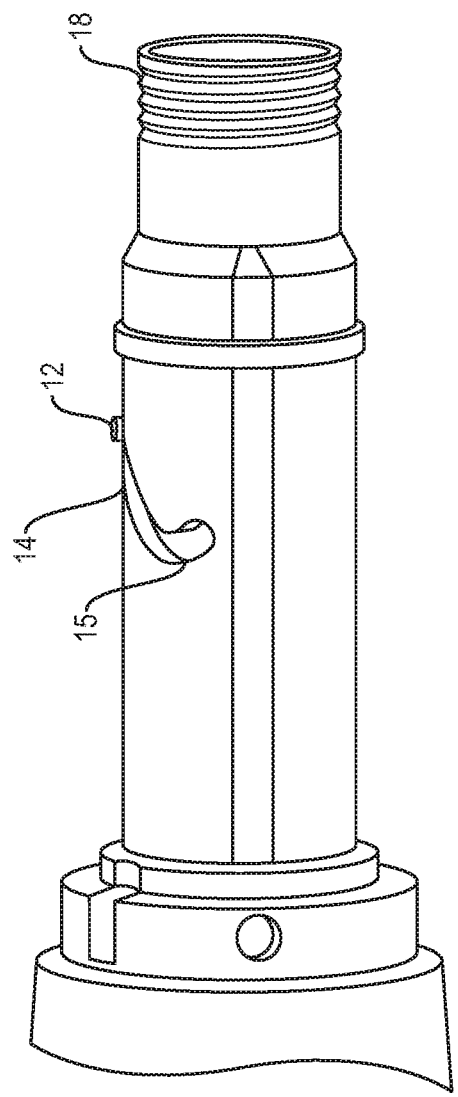
FIG. 8 is a schematic view of the initial position of the locking pin of the drive shaft of a working member in accordance with one aspect of the present disclosure.
Figure 9:
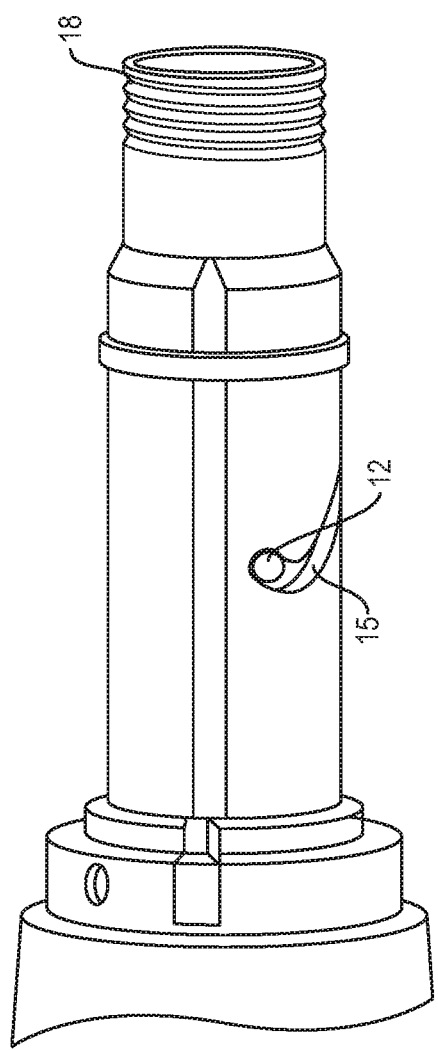
FIG. 9 is a schematic view of the locked position of the locking pin of the drive shaft of a working member in accordance with one aspect of the present disclosure.

FIG. 8 and FIG. 9 are schematic illustrations of one type of a distal end of the handpiece to illustrate how a locking ring as described herein may be employed to facilitate a locking pin 12 to lock and secure a drive shaft of a working member (the drive shaft not shown for simplicity). The locking pin 12 of FIG. 8 is at its initial position 14 where a drive shaft of the working member can be freely moved in or out of the distal end of the handpiece. Once the drive shaft is placed into a proper position, the locking ring (not shown) then comes into play: engaging the hidden slot of the locking ring with the locking pin 12, and rotating the locking ring to push the locking pin 12 all the way into a locking position 15 as shown in FIG. 9. Afterwards, the locking ring may be rotated to engage the short open slot to ensure the locking pin 12 at its locking position during an operation. More detailed information can also be found, for example, at FIG. 8, FIG, 9, and FIG. 10 of the US application publication No. 2015/0,313,610, and the entire contents of which are incorporated herein by reference. Additionally, the threaded distal end 18 of the handpiece as shown in FIG. 8 and FIG. 9 may be a preferable type for coupling with a threaded adaptor as described herein.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed:

1. A medical device comprising:
    an adaptor extending from a proximal end to a distal end along a longitudinal adaptor axis and having a slot and lock screw arrangement, the adaptor configured to be connectable to a handpiece; and
    an extension tube configured to be partially received within the adaptor, the extension tube configured to partially receive a drive shaft of a working member;
    wherein the slot and lock screw arrangement includes a linear slot extending in a direction generally parallel to the longitudinal adaptor axis and a lock screw configured to slide toward the distal end of the adaptor and toward the proximal end of the adaptor along the slot to adjust a longitudinal position of the lock screw; and
    wherein the slot and lock screw arrangement is configured to adjustably lock the extension tube along the drive shaft of the working member.

2. The medical device of claim 1, wherein the medical device further comprises a locking ring configured to receive a distal portion of the handpiece.

3. The medical device of claim 2, wherein the locking ring is configured to have one or more slots.

4. The medical device of claim 3, wherein the one or more slots are configured to work together with a locking pin to lock the drive shaft of the working member.

5. The medical device of claim 3, wherein the one or more slots comprise one set of open slots.

6. The medical device of claim 3, wherein the one or more slots comprise one set of hidden slots.

7. A medical device comprising:
    a handpiece;
    a locking ring that is separable from the handpiece, the locking ring including an inner passageway configured to receive a portion of the handpiece therethrough;
    an adaptor configured to be connectable to the handpiece, the adaptor extending from a proximal end to a distal end along a longitudinal adaptor axis and having a slot and lock screw arrangement, the slot and lock screw arrangement including a linear slot extending in a direction generally parallel to the longitudinal adaptor axis and a lock screw configured to slide toward the distal end of the adaptor and toward the proximal end of the adaptor along the slot to adjust a longitudinal position of the lock screw; and
    an extension tube configured to be partially received within the adaptor, the extension tube configured to partially receive a drive shaft of a working member,
    wherein the slot and lock screw arrangement is configured to adjustably lock the extension tube along the drive shaft of the working member.

8. The medical device of claim 7, wherein the locking ring is configured to have one or more slots.

9. The medical device of claim 8, wherein the one or more slots are configured to work together with a locking pin to lock the drive shaft of the working member.

10. The medical device of claim 8, wherein the one or more slots comprise one set of open slots.

11. The medical device of claim 8, wherein the one or more slots comprise one set of hidden slots.

12. A medical device comprising:
    a handpiece;
    a working member having a drive shaft, the drive shaft configured to be operably connectable to the handpiece;
    a locking ring configured to receive a portion of the handpiece;
    an adaptor having a slot and lock screw arrangement, the adaptor configured to be detachably connectable to the handpiece through a threaded coupling; and
    an extension tube configured to provide support for the drive shaft of the working member,
    wherein the slot and lock screw arrangement is configured to adjustably lock the extension tube along the drive shaft of the working member.

13. The medical device of claim 12, wherein the locking ring is configured to have one or more slots.

14. The medical device of claim 13, wherein the one or more slots is configured to work together with a locking pin to lock the drive shaft of the working member.

15. The medical device of claim 13, wherein the one or more slots comprise one set of open slots.

16. The medical device of claim 13, wherein the one or more slots comprise one set of hidden slots.

17. The medical device of claim 12, wherein the extension tube is configured to be partially received within the adaptor.

18. The medical device of claim 12, wherein the working member is a high speed drill bit or a high speed burr.

\* \* \* \* \*

UNITED STATES PATENT AND TRADEMARK OFFICE
CERTIFICATE OF CORRECTION

PATENT NO. : 11,376,023 B2
APPLICATION NO. : 15/993772
DATED : July 5, 2022
INVENTOR(S) : Ming J. Cheng It is certified that error appears in the above-identified patent and that said Letters Patent is hereby corrected as shown below:

On the Title Page

Item (73), in "Assignee", in Column 1, Line 1, delete "Gyms" and insert --Gyrus-- therefor Signed and Sealed this
Seventh Day of March, 2023

Katherine Kelly Vidal
*Director of the United States Patent and Trademark Office*